United States Patent [19]

Fukushima et al.

[11] Patent Number: 4,594,569
[45] Date of Patent: Jun. 10, 1986

[54] HUMIDITY SENSITIVE DEVICE

[75] Inventors: Fumio Fukushima, Miyazaki; Jiro Terada; Tsuneharu Nitta, both of Katano, all of Japan

[73] Assignee: Matsushita Electric Industrial Co., Ltd., Kadoma, Japan

[21] Appl. No.: 796,506

[22] Filed: Nov. 12, 1985

Related U.S. Application Data

[63] Continuation of Ser. No. 682,827, Dec. 19, 1984, which is a continuation of Ser. No. 462,974, Feb. 1, 1983, abandoned.

[30] Foreign Application Priority Data

Feb. 12, 1982 [JP] Japan ................... 57-21433
Mar. 12, 1982 [JP] Japan ................... 57-39826

[51] Int. Cl.$^4$ ............................................. H01L 7/00
[52] U.S. Cl. .......................... 338/35; 338/34; 324/65 R
[58] Field of Search ............... 338/35, 34; 324/65 R, 324/65 P; 73/27 R, 29, 335, 336.5; 252/520

[56] References Cited

U.S. PATENT DOCUMENTS

| | | |
|---|---|---|
| 3,478,573 | 11/1969 | King et al. . |
| 3,926,858 | 12/1975 | Ichinose et al. ............. 252/520 X |
| 4,011,538 | 3/1977 | Froemel . |
| 4,015,230 | 3/1977 | Nitta et al. ................... 338/35 |
| 4,017,820 | 4/1977 | Ross . |
| 4,080,564 | 3/1978 | Nitta et al. ................... 338/35 X |
| 4,086,556 | 4/1978 | Nitta et al. . |
| 4,326,414 | 4/1982 | Terada et al. ................ 73/336.5 |
| 4,378,691 | 4/1983 | Terada et al. ................ 73/27 R |
| 4,419,021 | 12/1983 | Terada et al. ............... 338/35 X |

FOREIGN PATENT DOCUMENTS 0013022 7/1980 European Pat. Off. .

Primary Examiner—Clarence L. Albritton
Assistant Examiner—M. M. Lateef
Attorney, Agent, or Firm—Cushman, Darby & Cushman

[57] ABSTRACT

A humidity sensitive device for sensing the humidity of an ambient humidity comprising a humidity sensitive resistor 15 which comprises as main component at least one selected from the group consisting of $ZrO_2$, $TiO_2$, $Nb_2O_5$ and $Ta_2O_5$ and an electric heater 13 applied near and for heating and retaining the humidity sensitive resistor 15 at a temperature above 200° C. The humidity sensitive resistor 15 and a fixed resistor are series connected across an AC voltage source 17, and a voltage across the humidity sensitive resistor 15 or the fixed resistor 16 is rectified by a AC/DC converter and compared with a reference voltage by a comparator, thereby an output responding to humidity in the atmosphere can be measured for a wide range of temperature.

9 Claims, 3 Drawing Figures

Absolute humidity
(weight %)

HUMIDITY SENSITIVE DEVICE

This is a continuation of application Ser. No. 682,827 filed Dec. 19, 1984, which is a continuation of Ser. No. 462,974 filed Feb. 1, 1983 which was abandoned upon the filing hereof.

BACKGROUND OF THE INVENTION

1. Field of the Invention

The present invention relates to a humidity sensitive device and humidity sensitive apparatus for use in detection of humidity in food cooking apparatus, dryer, air conditioner or measurement apparatus.

2. Description of the Prior Art

Generally speaking, metal oxides are superior in physisorption of water, and the amount of the physisorpted water depends on temperature and humidity of the atmosphere. When water is physisorpted on the surface of the metal oxide, ionic conduction will then increase thereby lowering the oxide's electrical resistance.

Most conventional humidity sensing devices utilize physisorption of water molecules on the surface of the above-mentioned metal oxide. Metal oxides such as $Fe_3O_4$, $Fe_2O_3$, $Cr_2O_3$, $Ni_2O_3$, $Al_2O_3$, $TiO_2$, $ZnO$, $MgCr_2O_4$, $TiO_2$-$V_2O_5$ compositions have been conventionally utilized and $ZnO$-$Cr_2O_3$-$Li_2O$-$V_2O_5$ compositions.

The conventional humidity sensitive device is capable of converting a humidity value an electrical resistance value, and thus by utilizing this characteristic various humidity sensing apparatuses have been devised.

Known uses for humidity sensing devices include air conditioners, food cooking apparatus, dryers and measurement apparatus.

However, the above-mentioned conventional humidity sensing device has the following problem. That is, the conventional humidity sensing device has a poor humidity-resistance characteristic against severe atmosphere and is thus limited to atmospheric temperature environments for humidity detection. The reason for the poor characteristic is that when dust or oil vapor is physisorpted onto the metal oxide surface, the physisorption of water changes. The reason for narrow atmospheric temperature detectability of humidity is that, above 100° C. the physisorption of water onto the metal oxide surface rapidly decreases and under the atmospheric temperature of 0° C., the water physisorpted on the metal oxide surface physically changes to an ice state.

In order to improve the above-mentioned atmospheric humidity-resistance characteristic, the sensitive device has previously been washed by organic solvent or heated under high temperatures to burn off the physisorpted substances. However, such conventional methods hinder continuous detection of humidity.

The above-mentioned shortcoming of the humidity sensitive device is a common problem in any device utilizing the principal of water physisorption.

Another type of atmosphere sensitive device is known however which does not utilize the physisorption of water. This known device detects gas by utilizing ceramic of $SnO_2$ composition. However, this conventional gas detection device comprising the $SnO_2$ ceramic detects reducing gas, and therefore when reducing gas exists in addition to humidity, then the sensitive device exhibits a considerable output. Accordingly, such a sensitive device cannot be used for accurate measurement of humidity alone in an atmosphere which may include reducing gas.

From the above-mentioned circumstancess there has been a great demand need for humidity sensing device which is sensitive only for a humidity, apart from reducing gas, in a wide range of atmospheric temperatures.

SUMMARY OF THE INVENTION

The purpose of the present invention is to provide a humidity sensing device and humidity sensing apparatus capable of sensing humidity over a wide range of atmospheric temperature without being influenced by dust and oil vapor in the atmosphere.

The humidity sensitive device in accordance with the present invention can measure humidity over a wide range of atmospheric temperatures by utilizing a humidity sensitive device which changes electrical resistance depending on the humidity at the temperature of the sensitive device of above 200° C., which temperature is maintained by an electric heater provided near the humidity sensing device.

A humidity sensitive device for sensing humidity of an ambiemt atmosphere comprises a humidity sensitive resistor, the resistance of which is dependent on humidity at a temperature substantially above 200° C., the humidity sensitive resistor containing as main component at least one substance selected from the group consisting of $ZrO_2$, $TiO_2$, $Nb_2O_5$ and $Ta_2O_5$ and an electric heater for heating the humidity sensitive resistor.

By heating the humidity sensitive device above 200° C., the resistance of the humidity sensitive device depends on atmospheric humidity at a high temperature, e.g., above 200° C., where the effect of physisorption becomes negligibly small.

Furthermore, due to the addition as an auxiliary component at least one substance selected from the group consisting of BeO, MgO, CaO, BaO, SrO, ZnO, CdO and $Al_2O_3$, the humidity sensing ability at high temperatures is further improved.

DESCRIPTION OF THE PREFERRED EMBODIMENTS

A humidity sensitive device and humidity sensitive apparatus in accordance with the present invention comprises a humidity sensitive resistor wherein electrical resistances responsive to humidity of the ambient atmosphere above 200° C. Even should dust or oil vapor be present in the ambient atmosphere they are not physisorpted on the surface of the humidity sensitive resistor since it is used at a raised temperature of above 200° C. Even should dust or oil vapor be physisorpted on the surface of the humidity sensitive resistor, they are rapidly burnt or vaporized and thus do not influence the humidity sensitivity of the resistor.

The humidity sensitive resistor in accordance with the present invention is a metal oxide ceramic containing at least one substance selected from the group consisting of $ZrO_2$, $TiO_2$, $Nb_2O_5$ and $Ta_2O_5$. The inventors herein have discovered that the above-mentioned humidity sensitive resistor changes electrical reistance only in dependence thereon of the humidity of the ambient atmosphere of above 200° C. The humidity sensitive resistor of the present invention changes its resistance responding to ambient humidity by means of chemisorption of water instead of physisorption of the conventional humidity sensitive device, and can detect humidity even in a high temperature atmosphere.

It have been experimentally determined that the temperature of the humidity sensitive resistor should be preferably above 200° C. The reason for this characteristic is that below 200° C. the device is likely to be influenced by physisorption of the water, and further, organic substances (for instance oil particle or dust included in smoke or the like) is likely to be absorbed under 200° C. Such absorption will cause error and instability during usage of the device, thereby preventing stable humidity detection for a long period of time.

Furthermore, should a reducing gas be included in the ambient atmosphere when humidity is measured, the temperature of the humidity sensitive resistor is preferably above 500° C. This is because under 500° C., by means of the existence of the reducing gas the electrical resistance changes and the measured humidity value produces error.

Furthermore, the measurement of the humidity through resistance change of humidity sensitive resistor should be preferably made by AC current. The reason why is that when a DC voltage is impressed on a humidity sensitive resistor at a raised temperature, migration of certain ionic components may occur, thereby producing a change of the device's characteristic.

Hereinafter the invention will be elucidated with respect to several examples as follows:

EXAMPLE 1

Figure 1:
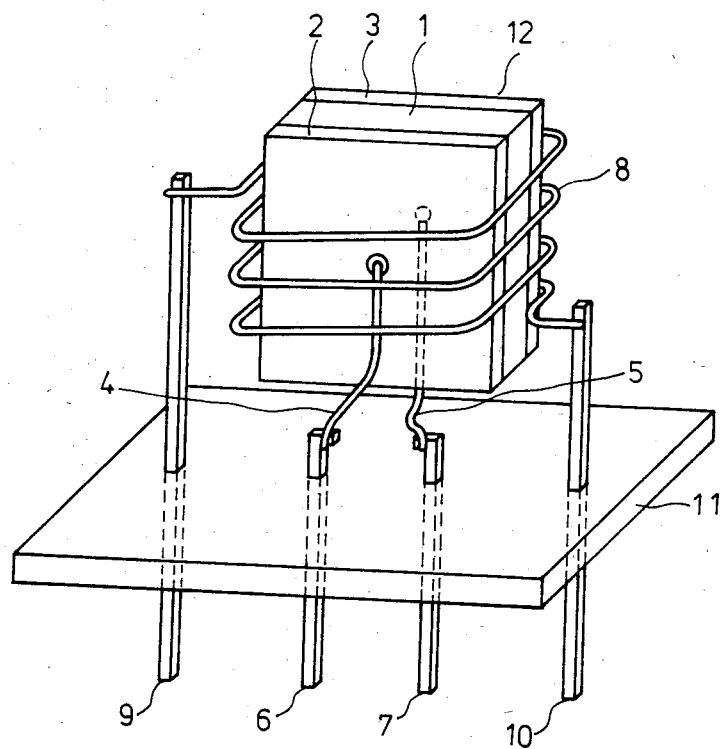
FIG. 1 is a perspective view of an example of a humidity sensitive apparatus in accordance with the present invention.
Figure 2:
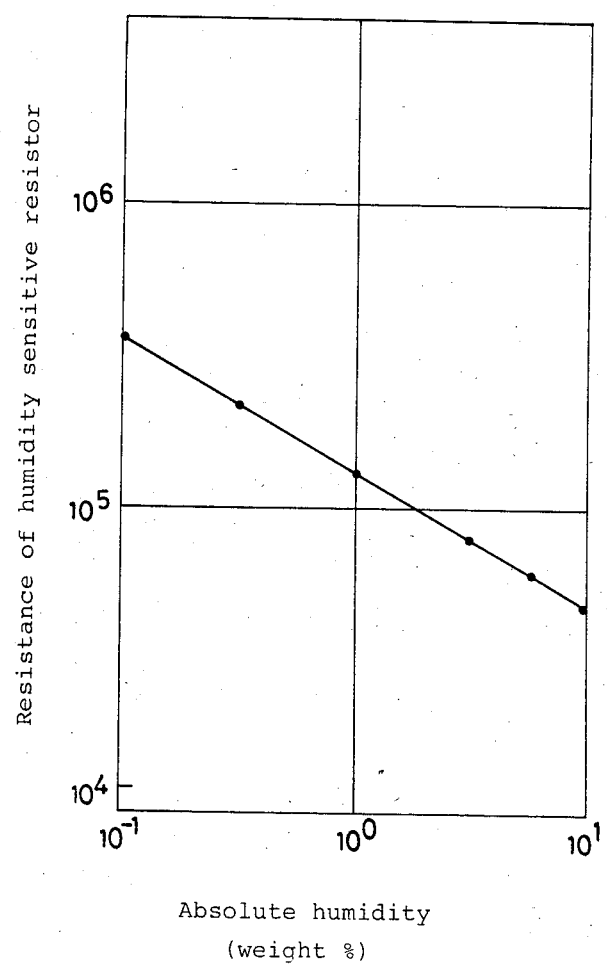
FIG. 2 is a graph showing the relationship between absolute humidity vs. resistance of the humidity sensitive resistor.

As a starting material for the humidity sensitive resistor, $ZrO_2$ powder of purity of above 99.9% is used. The material powder is pressed into a square plate of 5 mm×5 mm×0.5 mm by a pressure of 750 kg/cm$^2$. The resultant pressed plate is fired at 1300° C. in air for 2 hours. Thus a humidity sensitive resistor body 1 is formed. Then on both principal faces of the resistor body 1 a conductive paste comprising a composition mainly containing $RuO_2$ as glaze resistor paste is applied, and as widely known, is fired at about 800° C. to form the electrodes 2 and 3 as shown in FIG. 1. Then lead wires 4 and 5 are fire-bonded by using said conductive paste on the electrodes 2 and 3. The lead wires 4 and 5 are preferably Pt-Ir-alloy wires (Pt: 90%, Ir: 10%). The other ends of the lead wires 4 and 5 are connected to fixing terminals 6 and 7 of a base 11 by means of electric welding. Then an electric heating wire 8 of platinum coil is fixed around the above-mentioned humidity sensitive resistor 15 in an insulated manner thereto and both ends of the electric heater 8 are connected to terminals 9 and 10 by electric welding. The base or substrate 11 is made of insulating ceramic of metal oxide such as $Al_2O_3$ and holds the above-mentioned component. In the above-mentioned example of the humidity sensitive resistor the resistor 15 is heated and kept at 600° C. by applying DC current through the electric heater 8. The characteristic of the humidity sensitive resistor device of the above-mentioned example is shown in FIG. 2 wherein abscissa is graduated by absolute humidity (weight %) and the ordinate is graduated by resistance of humidity sensitive resistor. As shown in FIG. 2 the humidity sensitive resistor of the above example can stably and accurately measure the ambient humidity by heating and keeping it above 600° C. without undesirable influence of dust oil vapor and reducing gas (e.g. 0 to 3000 ppm concentration of ethyl alcohol) in the ambient atmosphere.

EXAMPLE 2-10

By using material powder of at least one selected from the group consisting of $ZrO_2$, $Nb_2O_5$ and $Ta_2O_5$ and in the same process as described in the preceding example 1, a humidity sensitive device is produced. Sensitivities corresponding to contents ratio of the materials of the examples 2-10 are shown in Table 1, the sensitivity of humidity measurement is defined by the following equation:

$$S = \log (R_1/R_0) \quad (1)$$

wherein $R_0$: resistance of the humidity sensitive resistor at 600° C. in dry air, $R_1$: resistance of the humidity sensitive resistor at 600° C. in an air containing 10 wt % of water gas.

TABLE 1

| Example | Contents (mol ratio) | Sensitivity |
|---|---|---|
| 2 | $ZrO_2$ | −0.66 |
| 3 | $Nb_2O_5$ | −0.48 |
| 4 | $Ta_2O_5$ | −0.49 |
| 5 | 0.9 $ZrO_2$—0.1 $Nb_2O_5$ | −0.72 |
| 6 | 0.5 $ZrO_2$—0.5 $Nb_2O_5$ | −0.68 |
| 7 | 0.1 $ZrO_2$—0.9 $Nb_2O_5$ | −0.65 |
| 8 | 0.9 $ZrO_2$—0.1 $Ta_2O_5$ | −0.75 |
| 9 | 0.1 $ZrO_2$—0.9 $Ta_2O_5$ | −0.70 |
| 10 | 0.4 $ZrO_2$—0.3 $Nb_2O_5$—0.3 $Ta_2O_5$ | −0.67 |

As shown in Table 1 the humidity sensitive device of the present invention has a good sensitivity at a high temperature. The humidity sensitive device manufactured in the above-mentioned examples can measure temperatures without undesirable influences from ambient atmosphere temperature, such as, oil vapor and reducing gases (e.g. 0–3000 ppm of ethyl alcohol) in ambient atmosphere, when heated and retained at a predetermined temperature (for instance 600° C.).

EXAMPLES 11-30

As a starting material, powder containing at least one main compound selected from the group consisting of $ZrO_2$, $Nb_2O_5$ and $Ta_2O_5$, and at least one sub-component selected from the group consisting of BeO, MgO, CaO, SrO, BaO, ZnO, CdO and $Al_2O_3$, and the humidity sensitive device is manufactured in the similar manner as that of the first example.

The characteristics of the resulting humidity sensitive devices corresponding to the contents of materials utilized are shown below in Table 2. Humidity sensitivity is defined by the same equation (1) as that in the preceding examples 2-10.

TABLE 2

| Example | Contents (mol ratio) | Sensitivity |
| --- | --- | --- |
| 11 | 0.9 $ZrO_2$—0.1 MgO | −0.70 |
| 12 | 0.8 $ZrO_2$—0.2 MgO | −0.72 |
| 13 | 0.7 $ZrO_2$—0.3 MgO | −0.72 |
| 14 | 0.6 $ZrO_2$—0.4 MgO | −0.70 |
| 15 | 0.3 $ZrO_2$—0.6 MgO | −0.65 |
| 16 | 0.9 $ZrO_2$—0.1 BeO | −0.68 |
| 17 | 0.9 $ZrO_2$—0.1 CaO | −0.66 |
| 18 | 0.9 $ZrO_2$—0.1 SrO | −0.68 |
| 19 | 0.9 $ZrO_2$—0.1 BaO | −0.69 |
| 20 | 0.9 $ZrO_2$—0.1 ZnO | −0.70 |
| 21 | 0.9 $ZrO_2$—0.1 CdO | −0.67 |
| 22 | 0.95 $ZrO_2$—0.05 $Al_2O_3$ | −0.79 |
| 23 | 0.9 $ZrO_2$—0.1 $Al_2O_3$ | −0.81 |
| 24 | 0.8 $ZrO_2$—0.2 $Al_2O_3$ | −0.80 |
| 25 | 0.9 $Nb_2O_5$—0.1 MgO | −0.60 |
| 26 | 0.9 $Nb_2O_5$—0.1 ZnO | −0.62 |
| 27 | 0.9 $Nb_2O_5$—0.1 $Al_2O_3$ | −0.68 |
| 28 | 0.9 $Ta_2O_5$—0.1 MgO | −0.58 |
| 29 | 0.9 $Ta_2O_5$—0.1 ZnO | −0.58 |
| 30 | 0.9 $Ta_2O_5$—0.1 $Al_2O_3$ | −0.54 |

As shown in Table 2 the humidity sensitive resistor of examples 11–30 exhibits good sensitivities at high temperature and sensitivities are increased as a result of adding the sub-components.

As is apparent from Table 2, the humidity sensitive devices of these examples can measure humidities without undesirable influences from ambient atmosphere temperature, thus, oil vapor and reducing gases (e.g. 0–3000 ppm of ethyl alcohol) in ambient atmosphere, when heated and retained at a predetermined temperature (for instance 600° C.).

EXAMPLES 31–39

As a starting material, powder containing $TiO_2$ as a main component and one substance selected from the group consisting of $TiO_2$, BeO, CaO, BaO, SrO, ZnO, CdO and $Al_2O_3$ is used and the humidity sensitive resistor is manufactured in a similar manner as that of example 1.

Humidity sensitive characteristics of the humidity sensitive devices of these examples corresponding to the components utilized are shown below in Table 3.

Humidity sensitivity is defined by the same equation (1) as in the preceding examples 2–10.

TABLE 3

| Example | Contents (mol ratio) | Sensitivity |
| --- | --- | --- |
| 31 | $TiO_2$ | +0.55 |
| 32 | 0.95 $TiO_2$—0.05 BeO | +0.67 |
| 33 | 0.95 $TiO_2$—0.05 CaO | +0.60 |
| 34 | 0.95 $TiO_2$—0.05 SrO | +0.70 |
| 35 | 0.95 $TiO_2$—0.05 BaO | +0.73 |
| 36 | 0.95 $TiO_2$—0.05 ZnO | +0.65 |
| 37 | 0.95 $TiO_2$—0.05 CdO | +0.72 |
| 38 | 0.95 $TiO_2$—0.05 $Al_2O_3$ | +0.91 |
| 39 | 0.95 $TiO_2$—0.05 MgO | +0.80 |

As shown in the Table 3 the humidity sensitive resistor of the examples 31–39 exhibits good sensitivities at high temperature and sensitivities are increased as a result of adding the sub-components.

As is evident from Table 3, the humidity sensitive devices of these examples can measure humidities without undesirable influences from ambient atmosphere temperature, thus, oil vapor and reducing gases (e.g. 0–3000 ppm of ethyl alcohol) in ambient atmosphere, when heated and retained at a predetermined temperature (for instance 600° C.).

EXAMPLE 40

Figure 3:
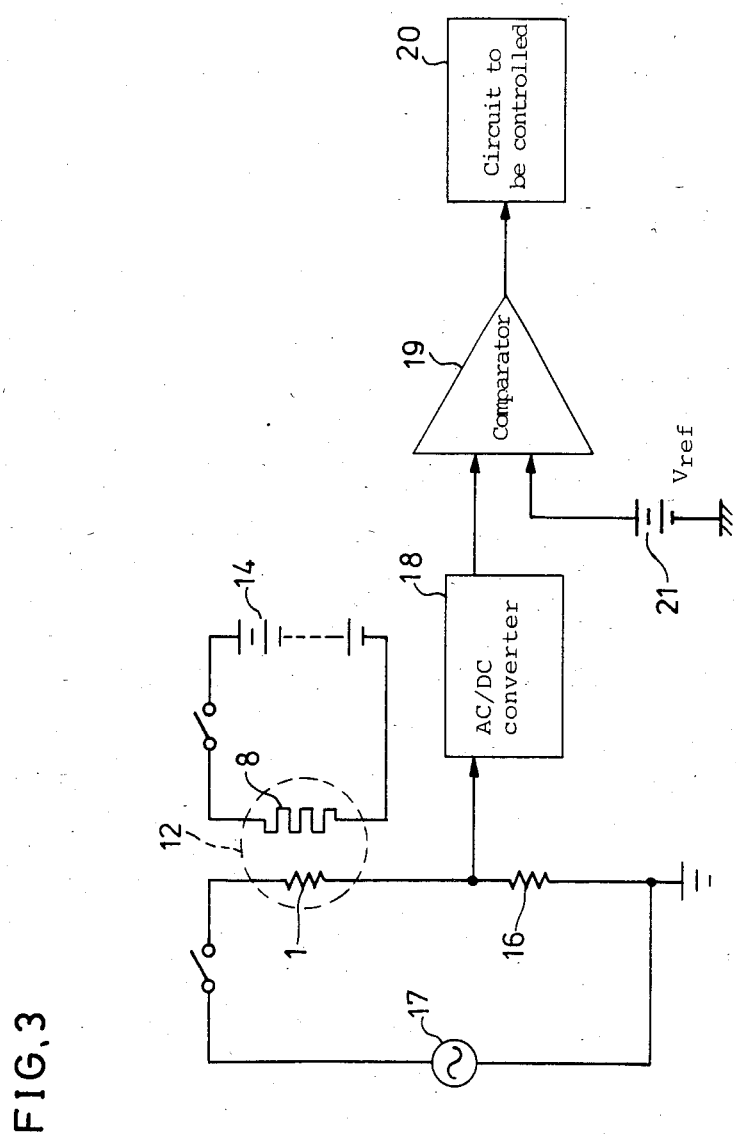
FIG. 3 is a circuit diagram of an example of the humidity sensitive apparatus embodying the present invention.

FIG. 3 shows a circuit block diagram of an example of humidity sensitive apparatus embodying the humidity sensitive device of the above examples. As shown in FIG. 3, the apparatus comprises a humidity sensitive device 12 which comprises a humidity sensitive resistor 1 and a heater 8 provided to heat the humidity sensitive resistor 1 in an insulated manner. The heater 8 is connected to a DC power source 14 and heats and keeps the humidity sensitive resistor 1 at a certain high temperature, e.g. about 600° C. As one example the humidity sensitive device 12 is the device manufactured in the preceding example 1.

The humidity sensitive resistor 1 is connected in series with a fixed resistor 16, thereby forming a voltage divider, which is connected across a an AC power source 17. Accordingly, an AC output voltage responding to the measured humidity is output across the fixed resistor 16. Then the output voltage at the junction point between the humidity sensitive resistor 1 and the fixed resistor 16 is impressed to an AC/DC convertor 18.

Then the output of the AC/DC conver 18 is given to the comparator 19, which comprises the output with a reference voltage given by a reference voltage source 21. The comparator 19 issues output signal to a circuit to be controlled 20. The reference voltage $V_{ref}$ should be suitably decided depending on the way and type of the circuit to be controlled 20.

FIG. 3 is only an example of a circuit of the humidity sensitive apparatus utilizing the humidity sensitive device in accordance with the present invention, and the circuit is not necessarily limited to that shown in FIG. 3.

Though the humidity sensitive resistor 12 in FIG. 3 is the one comprising $ZrO_2$ as main component, any other type of humidity sensitive resistor, for instance, that which comprises as main component one substance selected from the group consisting of $NiO_2$, $ZrO_2$, $Nb_2O_5$ and $Ta_2O_5$, and furthermore such sub-component as one substance selected from the group consisting of BeO, MgO, CaO, BaO, SrO, ZrO, CdO and $Al_2O_3$ may be used.

The above-mentioned humidity sensitive device in accordance with the present invention operates at a temperature above 200° C. and therefore (1) a very reliable high accuracy measurement can be made even in an ambient atmosphere containing dust or oil vapor or smoke, (2) the humidity measurement can be made continuously without interruption, (3) the humidity measurement can be made for a high temperature ambient atmosphere, and (4) the humidity measurement can be made even in an atmosphere containing at least one reducing gas by heating and keeping the humidity sensitive resistor to a high temperature, e.g. above 500° C.

What is claimed is:

1. A humidity sensitive device for sensing the humidity of an ambient atmosphere comprising:
humidity sensitive resistor means for exhibiting an electrical resistance which is dependent upon chemisorption of water vapor at a temperature substantially above 200° C. where substantially no physisorption is possible to thereby responsively sense the humidity of an ambient atmosphere during a humidity sensing operation conducted at said temperature;

said humidity sensitive resistor means consisting essentially of at least one main component selected from the group consisting of $ZrO_2$, $Nb_2O_5$, and $Ta_2O_5$; and electric heater means for maintaining said humidity sensitive resistor means at said temperature above 200° C. during said humidity sensing operation.

2. A humidity sensitive device in accordance with claim 1 wherein said humidity sensitive resistor means comprises as main component said at least one substance selected from the group consisting of $ZrO_2$, $Nb_2O_5$ and $Ta_2O_5$.

3. A humidity sensitive device in accordance with claim 2, wherein said humidity sensitive resistor further consists essentially of a sub-component of at least one substance selected from the group consisting of BeO, MgO, CaO, BaO, SrO, ZnO, CdO and $Al_2O_3$.

4. A humidity sensitive device for sensing the humidity of an ambient atmosphere comprising:

humidity sensitive resistor means for exhibiting an electrical resistance which is dependent upon chemisorption of water vapor at a temperature substantially above 200° C. to thereby responsively sense the humidity of an ambient atmosphere during a humidity sensing operation conducted at said temperature, said humidity sensitive resistor consisting essentially of at least one main component selected from the group consisting of $ZrO_2$, $Nb_2O_5$ and $Ta_2O_5$;

electric heater means fed with a controlled current for maintaining said humidity sensitive resistor means at said temperature substantially above 200° C. during said humidity sensing operation;

a resistor which is connected in a series to said humidity sensitive resistor thereby forming a voltage divider;

AC voltage source means for impressing a predetermined AC voltage across said voltage divider, means for measuring an AC output signal of said voltage divider and issuing an output responding to humidity of ambient atmosphere.

5. A humidity sensitive device in accordance with claim 4 wherein said humidity sensitive resistor means contains as main component said at least one substance selected from the group consisting of $ZrO_2$, $Nb_2O_5$ and $Ta_2O_5$.

6. A humidity sensitive device in accordance with claim 5 wherein said humidity sensitive resistor means further consists essentially of as sub-component at least one substance selected from the group consisting of BeO, MgO, CaO, BaO, SrO, ZnO, CdO and $Al_2O_3$.

7. A humidity sensitive device for sensing the humidity of an ambient atmosphere, comprising:

humidity sensitive resistor means having a metal oxide substrate and electrodes on one surface thereof, the resistivity of said humidity sensitive resistor means decreasing with an increase of the ambient humidity at a temperature above 200° C. to thereby responsively sense the humidity of an ambient atmosphere during a humidity sensing operation conducted at said temperature, wherein the effect due to water vapor physisorption becomes negligibly small at said temperature, said metal oxide substrate consisting essentially of, as solid ingredients, at least one main component selected from the group consisting of $ZrO_2$, $Nb_2O_5$ and $Ta_2O_5$; and heater means, positioned in proximity to and in isolated relation from said humidity sensitive resistor means, for maintaining said humidity sensitive resistor means at said temperature above 200° C. during said humidity sensing operation.

8. A humidity sensitive device in accordance with claim 7, wherein said metal oxide substrate further comprising, as solid ingredients, at least one sub-component selected from the group consisting of BeO, MgO, CaO, BaO, SrO, ZnO, CdO and $Al_2O_3$.

9. A humidity sensitive device according to claim 7, which further comprises; a fixed resistor coupled to said humidity sensitive resistor; a AC-DC converter coupled to said resistor for converting AC voltage to DC voltage; a comparator coupled to said converter for outputting a logic signal corresponding to the comparison between said DC voltage and a predetermined reference voltage; and a power source coupled to said heater for applying to said heater an electric power for keeping said humidity sensitive resistor at a temperature above 200° C.

* * * * *